US009282761B2

(12) United States Patent
Olofsson et al.

(10) Patent No.: US 9,282,761 B2
(45) Date of Patent: Mar. 15, 2016

(54) BACTERIA ISOLATED FROM FRESH HONEY OR THE HONEY PRODUCING TRACT OF HONEY BEES

(76) Inventors: Tobias Olofsson, Raa (SE); Alejandra Vasquez, Raa (SE)

( * ) Notice: Subject to any disclaimer, the term of this patent is extended or adjusted under 35 U.S.C. 154(b) by 1049 days.

(21) Appl. No.: 12/598,509

(22) PCT Filed: Apr. 30, 2008

(86) PCT No.: PCT/SE2008/000303
§ 371 (c)(1),
(2), (4) Date: Nov. 2, 2009

(87) PCT Pub. No.: WO2008/136730
PCT Pub. Date: Nov. 13, 2008

(65) Prior Publication Data
US 2010/0086528 A1    Apr. 8, 2010

Related U.S. Application Data

(60) Provisional application No. 60/916,809, filed on May 9, 2007.

(30) Foreign Application Priority Data

May 3, 2007    (SE) ...................................... 0701050

(51) Int. Cl.
| | | |
|---|---|---|
| C12N 1/20 | (2006.01) | |
| A23L 1/30 | (2006.01) | |
| A23K 1/00 | (2006.01) | |
| A61K 35/644 | (2015.01) | |
| A61K 35/745 | (2015.01) | |
| A61K 35/747 | (2015.01) | |
| C12R 1/01 | (2006.01) | |
| C12R 1/225 | (2006.01) | |

(52) U.S. Cl.
CPC .............. *A23L 1/3014* (2013.01); *A23K 1/009* (2013.01); *A61K 35/644* (2013.01); *A61K 35/745* (2013.01); *A61K 35/747* (2013.01); *C12R 1/01* (2013.01); *C12R 1/225* (2013.01); *A23V 2002/00* (2013.01)

(58) Field of Classification Search
None
See application file for complete search history.

(56) References Cited

U.S. PATENT DOCUMENTS

2006/0263344 A1    11/2006  Skop et al.

FOREIGN PATENT DOCUMENTS

JP          2222654 A       9/1990

OTHER PUBLICATIONS

Scardovi et al. (Arch. Mikrobiol. 72, 318-325 (1970)).*
Rada et al., Apidologie 1997;28:357-65.*
Halper et al., Experimental Biology and Medicine 2003, 228:1329-1337.*
Reid et al., FEMS Immunology and Medical Microbiology 35 (2003) 131-134.*
http://www.uniprot.org/taxonomy/1629, accessed Oct. 15, 2012.*
Evans et al., J. Econ. Entomol. 97(3): 752-756 (2004).*
Ruiz-Argueso, T. et al., "Microbiology of Ripening Honey", Applied Microbiology Dec. 1975.
Jeyaprakash, A. et al., "Bacterial diversity in worker adults of Apis mellifera capensis and Apis mellifera scutellata (Insecta: Hymenoptera) assessed using 16S rRNA sequences", Journal of Invertebrate Pathology 2003, vol. 84.
Forum on Microbial Threats, Ending the War Metaphor: The Changing Agenda for Unraveling the Host-Microbe Relationship-Workshop summary 2005, p. 243-244 and 252—& Database EMBL [Online] Accession No. AY667698, Feb. 1, 2005, retrieved from EBI.
Mundo, M. A. et al., 61C-11, 'Antimicrobial activity of honey against food pathogens and food spoilage microorganisms', Session 61C, Food Microbiology; General 1, 2002 Annual Meeting and Food Expo—Anaheim, California, p. 1 [online] Aug. 22, 2008 [retrieved on Sep. 1, 2008] Retrieved from the Internet: http://ift.confex.com/ift/2002/techprogram/paper_11581.htm.
Taormina, P. J. et al., "Inhibitory activity of honey against foodborne pathogens as influenced by the presence of hydrogen peroxide and level of antioxidant power", International Journal of Food Microbiology 2001, vol. 69.
Gilliam, M., 'Identification and roles of non-pathogenic microflora associated with honey bees', FEMS Microbiology Letters 1997, vol. 155.
Evans, J.D. et al., "Apiculture and Social Insects, Bacterial Probiotics Induce an Immune Response in the Honey Bee (Hymenoptera: Apidae)", Journal of Economic Entomology 2004, vol. 97, No. 3.
Edwards, C.G. et al., "*Lactobacillus kunkeei* sp. nov.: a spoilage organism associated with grape juice fermentations", Journal of Applied Microbiology 1998, vol. 84.
Olofsson et al., "Detection and Identification of a Novel Lactic Acid Bacterial Flora Within the Honey Stomach of the Honeybee *Apis mellifera*," Curr Microbiol (2008) 57:356-363.
Vásquez et al., "Symbionts as Major Modulators of Insect Health: Lactic Acid Bacteria and Honeybees," PLoS ONE, Mar. 2012, vol. 7, Issue 3, 9 pages.
Tamarit et al., "Functionally Structured Genomes in Lactobacillus kunkeei Colonizing the Honey Crop and Food Products of Honeybees and Stingless Bees," Genome Biol. Evol. 7(6): 1455-1473, Apr. 28, 2015.
Vásquez et al., "The lactic acid bacteria involved in the production of bee pollen and bee bread," Journal of Apicultural Research and Bee World, 48(3): 189-195 (2009).
Vásquez et al., "A scientific note on the lactic acid bacterial flora in honeybees in the USA—A comparison with bees from Sweden," Apidologie 40 (2009) 26-28.
Anderson et al., "Hive-stored pollen of honey bees: many lines of evidence are consistent with pollen preservation, not nutrient conversion," Molecular Ecology (2014) 23, 5904-5917.

* cited by examiner

*Primary Examiner* — Irene Marx
(74) *Attorney, Agent, or Firm* — Volpe and Koenig, P.C.

(57) ABSTRACT

The invention relates to new isolated *Lactobacillus* and *Bifidobacterium* strains which have been isolated from fresh honey having a water content above 18% by weight or from the honey producing tract of at least one bee. The bacterial strains have unique properties rendering them useful in many products such as in food and beverage products, feed products and medica products.

8 Claims, 4 Drawing Sheets

BACTERIA ISOLATED FROM FRESH HONEY OR THE HONEY PRODUCING TRACT OF HONEY BEES

FIELD OF INVENTION

The invention relates to new isolated *Lactobacillus* and *Bifidobacterium* strains. The invention further relates to compositions and products comprising these strains.

BACKGROUND OF INVENTION

Honey, the mysterious food used in medicine since ancient ages has puzzled people for centuries with it's healing effects on humans wounds documented already by the Egyptians 2000 B.C.

Honey is produced by bees such as the honey bee *Apis mellifera*. The nectar bees collect from plants is a sweet liquid mostly composed of sucrose. By the time the bee returns to the hive, much of the sucrose is converted to glucose and fructose. Honey further contains proteins, vitamins and minerals.

Presently, honey's therapeutic properties besides osmolarity and acidity, are explained by the hydrogen peroxide content as an action of peroxidase oxidase (White, et al. 1963 *Biochem Biophys Acta* 73, 57-70), the origin of the nectar by it's different flavonoid and phenolic acids content (Taormina, et al. 2001. *Int J Food Microbiol* 69(3), 217-225; Wandan, H. A. 1998. *Infection* 26(1), 26-31), and an unidentified component (Molan, P. C. 2001. World Wide Wounds (online); Available from URL: http://www.worldwidewounds.com/2001/november/Molan/honey-as-topical-agent.html). Despite scientific efforts performed during the last 30 years (Lusby, P. E., et al. 2005 *Arch Med Res* 36(5), 464-467; Molan, P. C. 2006. *Int J Low Extrem Wounds* 5(1), 40-54 *Int J Low Extrem Wounds* 5(2), 122; Mundo, M. A., et al. 2004 *Int J Food Microbiol* 1, 97(1), 1-8) the mystery regarding many of honey's modes of action still remains to be solved.

The antimicrobial properties possessed by honey render honey suitable for use in the dressing of wounds, where it assists in preventing infection, the debridement of necrotic tissue, the deodorising of malodorous wounds and the minimisation of scar formation. Honey containing wound and skin caring products are known through WO2004000339 and WO03047642.

In medical practice today antibiotics are most commonly used for treating infections. The extensive use of antibiotics have however led to antibiotic resistant pathogenic bacteria becoming a big problem. In food industry preservatives are extensively used in order to prolong the shelf life of food and prevent the growth of harmful pathogenic microorganisms. People are however becoming aware about the side effects of additives in food, such as allergies, and there is a growing demand for more natural food. These facts have led to an interest in traditional medicine and an urge to find new treatment solutions and preventive treatments and additives based on old wisdom.

An object of the invention is to obtain medical, food and feed products lending their beneficial properties from honey.

A further object is to synthetically produce honey.

Another object is to obtain new bacterial strains having antimicrobial activity.

SUMMARY OF THE INVENTION

These objects have now been fulfilled according to the present invention by providing new isolated *Lactobacillus* and *Bifidobacterium* strains which have been isolated from fresh honey having a water content above 18% by weight or from the honey producing tract of at least one bee, and compositions and products comprising these strains and a method of producing honey. There are further provided a method for the isolation of the bacterial strains.

Thus, the present inventors have found the bacterial strains closely involved in the production of honey. The bacterial strains have unique properties rendering them useful in many products such as medical products, food products, beverage products and feed products. The isolated bacterial strains grow quickly, at a low temperature and in an acid environment and are able to grow in highly concentrated sugar solutions. The bacterial strains can efficiently combat other organisms, especially organisms that are food spoiling and that are pathogenic for humans (such as *Listeria, Bacillus* and *Staphylococcus* species) and honeybees (such as *Paenibacillus larvae*). With a unique honey-related origin, the bacterial strains are well suited to be used in honey containing products. These products have unique health promoting properties.

Bacterial strains have not, up till now, been isolated from fresh honey or the honey producing tract of a bee. The honey producing tract of a bee entails the trunk, mouth, esophagus and honey sac of a honey producing bee, such as *Apis* spp. Thus, the gut or intestine is not part of the honey producing tract of a bee. Fresh honey is honey having a water content above 18% by weight, preferably above 20% by weight. Honey having a water content below 18% by weight is ripened honey, i.e. the honey normally consumed.

*Lactobacillus kunkeei* have appeared in the literature in relation to bees. One report relates to the examination of the microbial ecology of a social wasp *Vespula germanica* larval guts (Reeson, A. F., et al. 2003 *Insect Mol Biol* 12(1), 85-91), and a second report relates to as a single clone in a solitary bee *Osmia bicornis* larval intestinal flora (Mohr, K. I. and Tebbe, C. C. 2006. *Environ Microbiol* 8(2), 258-272). These two organisms lack a honey producing tract, do not produce honey and are therefore not honey bees.

Bee diseases are infections and parasitic conditions concerning enormous agriculture economics loss. The *Paenibacillus larvae* causing the American Foul Brood disease (AFB) is considered as one of the most dangerous pathogens for honey bees resulting in destruction of infected colonies in many countries (Genersch, E., et al. 2005. *Appl Environ Microbiol* 71(11), 7551-7555). JP2222654 suggests the use of *Lactobacillus* species from the intestine of honey bees in a feed for enhancing the immunological function of honey bees. These species of bacteria are isolated from the intestine of the honey bee and thus are not adapted to a honey-like environment.

JP 2222654 discloses *Lactobacillus bifidus* isolated from the intestine of a honey bee. The document further discloses feed for bees containing this bacteria as well as *Lactobacillus lactis* (i.e. animalis), *Streptococcus lactis, Bacillus subtilis* for stimulation of the intestine of honey bees.

A first aspect the of the invention relates to an isolated bacterial strain of the genus *Lactobacillus* or *Bifidobacterium*, isolated from fresh honey having a water content above 18% by weight or from the honey producing tract of at least one bee.

A second aspect of the invention relates to a composition comprising an isolated bacterial strain of the genus *Lactobacillus* or *Bifidobacterium*, isolated from fresh honey having a water content above 18% by weight or from the honey producing tract of at least one bee, wherein said composition may be a pharmaceutical composition.

A third aspect relates to a medical product comprising a pharmaceutical composition as outlined above.

A fourth aspect of the invention relates to a food or feed product comprising an isolated bacterial strain of the genus *Lactobacillus* or *Bifidobacterium*, isolated from fresh honey having a water content above 18% by weight or from the honey producing tract of at least one bee.

A fifth aspect of the invention relates to the use of an isolated bacterial strain of the genus *Lactobacillus* or *Bifidobacterium*, isolated from fresh honey having a water content above 18% by weight or from the honey producing tract of at least one bee for preparing a medical product, food product, beverage product or pharmaceutical composition for preventing and/or treating infections or gastrointestinal diseases.

A sixth aspect of the invention relates to a bacterial strain selected from the group consisting of *Lactobacillus* strain Biut2 (LMG P-24094), *Lactobacillus* strain Hma2 (LMG P-24093), *Lactobacillus* strain Hma8 (LMG P-24092), *Lactobacillus* strain Bma5 (LMG P-24090), *Lactobacillus* strain Hon2 (LMG P-24091) said strains being deposited at BCCM/LMG Bacteria Collection in Belgium on 3 Apr. 2007, *Bifidobacterium* strain Bin7 (LMG P-23986), *Bifidobacterium* strain Hma3 (LMG P-23983), *Bifidobacterium* strain Bin2 (LMG P-23984), *Bifidobacterium* strain Bma6 (LMG P-23985) and *Lactobacillus kunkeei* Fhon2 (LMG P-23987), said strains being deposited at BCCM/LMG Bacteria Collection in Belgium on 15 Jan. 2007 and Hma11 deposited at BCCM/LMG Bacteria Collection in Belgium.

A seventh aspect relates to a method for producing honey comprising adding at least one bacterial strain of the genus *Lactobacillus* or *Bifidobacterium*, isolated from fresh honey having a water content above 18% by weight or the honey producing tract of at least one bee, to a sugar source.

An eighth aspect of the invention relates to a method for isolation of a bacterial strain according to the invention comprising: a) sampling fresh honey having a water content above 18% by weight, or separating the honey producing tract from a bee and shaking the tract in a sterile medium; b) bacterial cultivation of the sample from a) on a suitable medium; c) pure culturing and isolation of bacterial strain(s) obtained in b) on a suitable medium.

Further advantages and objects of the present invention will be described in more detail, inter alia with reference to the accompanying drawings.

DETAILED DESCRIPTION OF THE INVENTION

Figure 1:
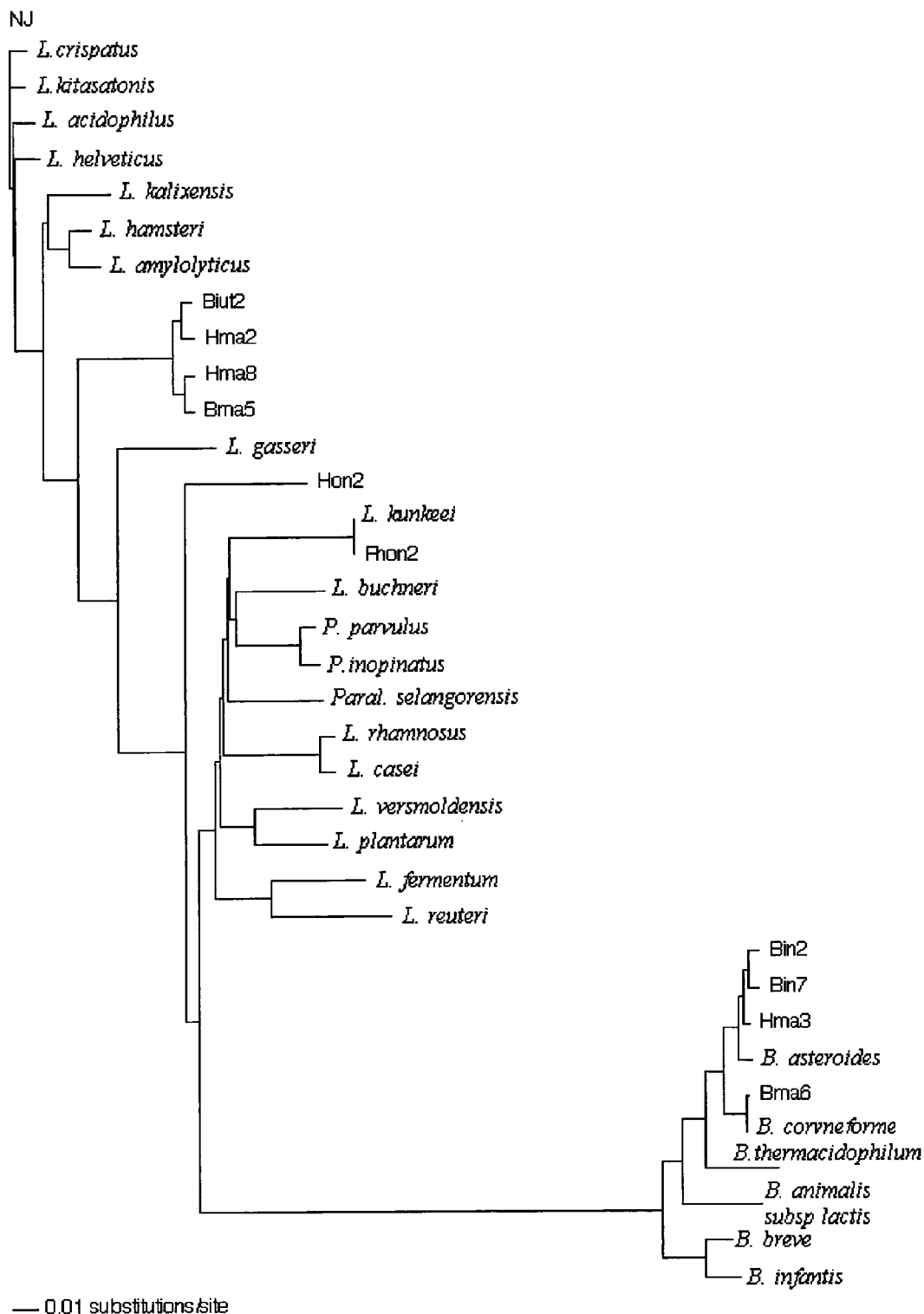
FIG. 1 illustrates a phylogenetic tree including the bacterial strains according to the invention.

The Application refers to biological material that was accepted for deposit under the Budapest Treaty with the Belgian Coordinated Collections of Microorganisms/Laboratorium voor Microbiologie-Bacterienverzammeling (BCCM/LMG), Universiteit Gent, K.L. Ledeganckstraat 35, B-0999 Gent, Belgium, and given the following deposit information:

| BCCM/LMG Accession No. | Description of Deposited Biological Material | Date of Deposit |
| --- | --- | --- |
| LMG P-24090 | *Lactobacillus* strain Bma5 | Apr. 3, 2007 |
| LMG P-24091 | *Lactobacillus* strain Hon2 | Apr. 3, 2007 |
| LMG P-24092 | *Lactobacillus* strain Hma8 | Apr. 3, 2007 |
| LMG P-24093 | *Lactobacillus* strain Hma2 | Apr. 3, 2007 |
| LMG P-24094 | *Lactobacillus* strain Biut2 | Apr. 3, 2007 |
| LMG P-23983 | *Bifidobacterium* strain Hma3 | Jan. 15, 2007 |
| LMG P-23984 | *Bifidobacterium* strain Bin2 | Jan. 15, 2007 |
| LMG P-23985 | *Bifidobacterium* strain Bma6 | Jan. 15, 2007 |
| LMG P-23986 | *Bifidobacterium* strain Bin7 | Jan. 15, 2007 |
| LMG P-23987 | *Lactobacillus kunkeei* Fhon2 | Jan. 15, 2007 |
| LMG P-24612 | Hma11 | Apr. 28, 2008 |

DEFINITIONS

In the context of the present application and invention, the following definitions apply:

The term "honey" means the sweet, viscous liquid produced in the honey producing tract of various bees from the nectar of flowers.

The term "bacteriocin" relates to an antibacterial substance produced by a bacteria. Bacteriocins are biologically active proteins or protein complexes (protein aggregates, lipocarbohydrate proteins, glycoproteins, etcetera) displaying a bacteriocidal mode of action towards closely related microorganisms. Several bacteriocins produced by lactic acid bacteria are active against food spoilage and food-borne pathogenic microorganisms.

The term "sugar source" means in general a sweet soluble disaccharide or small oligosaccharide carbohydrate. Examples of sugar sources are honey, sugar, glucose, fructose, sucrose and maltose.

The term "CFU" means colony-forming unit.

The term "lactic acid bacteria, LAB" relates to bacteria producing lactic acid, such as bacteria belonging to the genera *Lactobacillus*, *Lactococcus* and *Bifidobacterium*.

The term "probiotic microorganism" refers to a microorganism that form at least a part of the transient or endogenous flora and thereby exhibit a beneficial prophylactic and/or therapeutic effect on the host organism.

The term "molecular marker" is intended to mean a stretch of a nucleotide sequence, which may be used to identify a bacterial strain or related bacterial strains. The molecular marker may be used in hybridisation assays as well as in amplification assays such as in PCR.

The term "excipient" means any non-active ingredient added to a product or composition.

In this specification, unless otherwise specified, "a" or "an" means "one or more".

Honey Bee Specific Bacterial Strains

The invention relates to an isolated bacterial strain of the genus *Lactobacillus* or *Bifidobacterium*, isolated from the honey producing tract of at least one bee or from fresh honey having a water content above 18% by weight. An isolated bacerial strain entails at least one strain and thus may entail one or more bacterial strains. The honey producing tract of a bee may be further defined as consisting of the trunk, mouth, esophagus and honey sac, thus excluding the gut or intestine. The bee is preferably from the honey producing bee *Apis* spp, preferably *Apis mellifera*. The term "fresh honey" may be defined as honey not older than three days after the gathering of nectar by a honey bee to the beehive. Furthermore, "fresh honey" may preferably have a water content above about 20% by weight and may reside in not yet wax sealed cells. The water content of nectar, the raw material for the production of natural honey, collected by the bees may be up to 93% by weight. Normally the water content in nectar may be around 30-50% by weight. In contrast, ripened honey has got a water content below about 18% by weight.

The strain has preferably the ability to be viable for at least 8 days in a 65% by weight sugar solution, preferably 8 days in a 70% by weight sugar solution, which is of great importance in many industrial applications. The bacterial strain according to the invention may have the ability to inhibit the growth of food spoilage and pathogenic microorganisms, such as *Staphylococcus* species, *Listeria* species, *Clostridium* species, *Pseudomonas* species, *Escherichia coli*, *Saccharomyces cerevisiae* and *Paenibacillus larvae*.

A bacterial strain according to the invention may preferably be selected from the group consisting of *Lactobacillus* strain Biut2 (LMG P-24094), *Lactobacillus* strain Hma2 (LMG P-24093), *Lactobacillus* strain Hma8 (LMG P-24092), *Lactobacillus* strain Bma5 (LMG P-24090), *Lactobacillus* strain Hon2 (LMG P-24091) said strains being deposited at BCCM/LMG Bacteria Collection in Belgium (Universiteit Gent, K.L. Ledeganckstraat 35, B-0999 Gent, BELGIUM) on 3 Apr. 2007, *Bifidobacterium* strain Bin7 (LMG P-23986), *Bifidobacterium* strain Hma3 (LMG P-23983), *Bifidobacterium* strain Bin2 (LMG P-23984), *Bifidobacterium* strain Bma6 (LMG P-23985) and *Lactobacillus kunkeei* Fhon2 (LMG P-23987), said strains being deposited at BCCM/LMG Bacteria Collection in Belgium on 15 Jan. 2007 and Hma11 deposited at BCCM/LMG Bacteria Collection in Belgium before the filing of this application.

The composition according to the invention comprises an isolated bacterial strain of the genus *Lactobacillus* or *Bifidobacterium*, isolated from fresh honey having a water content above 18% by weight or from the honey producing tract of at least one bee. The composition comprise at least one bacterial strain or a mixture of several bacterial strains. The composition may further comprise a sugar source, preferably selected from the group consisting of honey, sugar, fructose, sucrose, dextrine, maltose or glucose. The composition may be a food product, that may prevent gastrointestinal diseases, such as synthetically produced honey produced by using the strain according to the invention or a food product comprising the strain such as a beverage product. The food or beverage can be used as a probiotic, prebiotic or symbiotic composition or product. The composition may further be a feed product such as a bee feed product.

The composition may be a pharmaceutical composition, that may prevent and/or treat infections or gastrointestinal diseases, comprising a pharmaceutically acceptable carrier and/or diluent. The pharmaceutical composition may be in the form of a suspension, gel, cream, powder or capsule.

A pharmaceutical product according to the invention comprise an isolated bacterial strain of the genus *Lactobacillus* or *Bifidobacterium*, isolated from fresh honey having a water content above 18% by weight or from the honey producing tract of at least one bee, that may prevent and/or treat infections or gastrointestinal diseases, and may be in the form of a dressing, bandage or spray.

The method for producing a composition according to the invention comprise adding at least one bacterial strain according to the invention to a sugar source. The sugar source may preferably be selected from the group consisting of honey, sugar, fructose, sucrose, dextrine, maltose or glucose. Such method may be the production of synthetic honey, wherein said at least one strain are allowed to ferment at least part of a sugar source.

These above mentioned compositions and products may contain live, freeze dried or killed bacteria. Further, they may contain metabolites and/or bacteriocins produced by the bacteria. A product containing freeze dried bacterial strains can be activated by the addition of water.

The method for isolation of a bacterial strain according to the invention comprise: a) sampling fresh honey having a water content above 18% by weight, or separating the honey producing tract from a bee and shaking the tract in a sterile medium; b) bacterial cultivation of the sample from a) on a suitable medium; c) pure culturing and isolation of bacterial strain(s) obtained in b) on a suitable medium. The honey producing tract is preferably separated after the oesophagus and before the proventriculous in order to avoid contamination from the gut or intestine. The method may further comprise: d) evaluating the ability of the strain(s) to inhibit food spoilage and pathogenic microorganisms.

The media for the cultivation may be selected from honey based agar, Tryptone Soy Broth agar (TSB) (such as from Oxoid, Basingstoke, Hampshire, England), Tomato juice agar (TJ) (such as from Oxoid), all purpose medium with Tween® (APT) (such as from Merck, Darmstadt, Germany) and Rogosa agar (such as from Merck).

Preferred bacterial strains according to the invention are disclosed in Table 1. The bacterial strains are catalase negative, gram-positive, non-sporulating and lactic acid producing rods complying with the taxonomic designation of *Lactobacillus* sp. and *Bifidobacterium* sp. They are also fast growing and have strong pathogen inhibiting properties. Further, the bacterial strains according to the invention are not harmful to humans.

TABLE 1

Isolated bacterial strains

| Bacteria | strain | Accession number BCCM/LMG |
|---|---|---|
| *Lactobacillus kunkeei* | Fhon2 | LMG P-23987 |
| *Lactobacillus* sp. | Hon2 | LMG P-24091 |
| *Lactobacillus* sp. | Biut2 | LMG P-24094 |
| *Lactobacillus* sp. | Hma2 | LMG P-24093 |
| *Lactobacillus* sp. | Hma8 | LMG P-24092 |
| *Lactobacillus* sp. | Bma5 | LMG P-24090 |
| *Lactobacillus* sp. | Hma11 | LMG P-. . . |
| *Bifidobacterium* sp. | Bin7 | LMG P-23986 |
| *Bifidobacterium* sp. | Hma3 | LMG P-23983 |
| *Bifidobacterium* sp. | Bin2 | LMG P-23984 |
| *Bifidobacterium* sp. | Bma6 | LMG P-23985 |

The bacterial strains listed in table 1 were deposited at the BCCM/LMG Bacteria Collection in Belgium in accordance with international deposits under the Budapest Treaty. A phylogenetic analysis where the 16S rRNA sequences of the strains were compared with other lactic acid bacterial strains confirmed that the isolated strains belong to the *Lactobacillus* and *Bifidobacterium* genus. As further specified in the examples nearly complete sequences of the 16S rRNA gene were determined and the sequences were used to search for 16S rRNA sequence similarities in the database Ribosomal Database Project (RDP) (Cole, J. R., et al. 2005. *Nucleic Acids Res* 1,33). This database is used for identification of bacteria by their 16S rRNA genes. Comparison of 16S rRNA sequences, which are highly conserved among all organisms, may be used to assess the phylogenetic relationship between organisms.

FIG. 1 discloses a phylogenetic tree based on distance matrix analysis of about 1400 positions in the 16S rRNA genes. The tree was constructed using the Neighbor joining method and evolutionary distances were estimated using the Log Det/Paralinear method in PAUP. Abbreviations: (B.) *Bifidobacterium*, (L.) *Lactobacillus*, (P.) *Pediococcus*, (Paral.) *Paralactobacillus*. Type strain numbers: *L. buchneri* JCM1115, *L. helveticus* DSM 20075, *L. crispatus* ATCC 33820, *L. gasseri* ATCC 33323, *L. versmoldensis* KU-3, *L. kalixensis* DSM 16043, *Paral. selangorensis* LMG 17710, *P. parvulus* JCM 5889, *P. inopinatus* DSM 20285, *L. kitasatonis* JCM 1039, *L. hamsteri* DSM 5661, *L. amylolyticus* DSM 1664, *L. kunkeei* YH-15, *B. thermacidophilum* subsp. *porcinum* P3-14, *B. asteroides* ATCC 25910, *B. coryneforme* ATCC 25911, *L. acidophilus* DSM 20079, *L. rhamnosus* JCM 1136, *L. plantarum* JCM 1149, *L. casei* JCM 1134, *L. fermentum* ATCC 14931, *L. reuteri* DSM 20016, *B. animalis* subsp. *lactis* DSM 10140, *B. breve* ATCC 15700, *B. infantis* ATCC 15697.

*Lactobacilli* strains Biut2, Hma2, Hma8 and Bma5 are new species within the *Lactobacillus* genus as depicted by the phylogenetic tree. These bacterial strains constitute a cluster with no other closely relatives within *Lactobacillus*. The cluster is allocated within the *L. delbrueckii* phylogenetic group.

*Lactobacillus* Hon2 constitutes a second cluster with a new species within the *Lactobacillus* genus. However, this cluster is allocated in between the *Lactobacillus casei-Pediococcus* phylogenetic group and the *L. delbrueckii* phylogenetic group. The 16S rRNA gene sequence of *Lactobacillus kunkeei* Fhon2 is identical to a previously described *Lactobacillus kunkeei* type strain and situated within the *Lactobacillus casei-Pediococcus* phylogenetic group. However, when the whole DNA of the microorganisms are compared, see FIG. 2, it is obvious that these two organisms do not correspond to each other.

Bifidobacteria Bin2, Hma3 and Bin7 are related to *Bifidobacterium asteroides* and could be assigned as strains within this species or as new species within the *Bifidobacterium* genus. Bifidobacteria Bma6 is closely related to *Bifidobacterium coryneforme*.

Hma11 is also a new species within the *Lactobacillus* genus.

The bacterial strains in table 1 have been identified to be honey bee specific, found in the honey producing tract of the honey bee or in fresh honey. The strains are transferred to the honey from the honey producing tract of the bee during the honey production. *Bifidobacterium* strain Bin2, *Lactobacillus* strain Hon2 and *Lactobacillus kunkeei* Fhon2 have also been found in fresh honey. When the water content in the honey decreases below about 18% no non-sporulating bacteria will survive, and thus the isolation of bacteria will be impossible. The honey will after 3-7 days contain dead bacteria and bacterial components such as bacteriocins and metabolites.

The bacterial strains according to the invention have a relatively low temperature range for optimal growth, between from about 20-35° C., such as between about 21-32° C., which is the temperature in the honey sac when honeybees gather nectar. Further, in contrast to many other lactic acid bacteria the bacterial strains grow quickly. They are also tolerant to acid environments such as between pH 2-5, which is the pH of naturally occurring honey.

The isolated *Lactobacilli kunkeei* Fhon2 is a facultative anaerobe, weakly catalase-positive, produces gas from glucose, utilizes citrate or malate in the presence of glucose, and produces mannitol from fructose. In addition, most of the time it does not produce ammonia from arginine nor reduces nitrate. Moreover, it ferments fructose, glucose, sucrose and raffinose.

The bacterial strains according to the invention are able to grow on media as tomato juice agar with possible addition of one or more of APT agar, Rogosa and Tryptic soy broth (TSB) agar, see the examples. The application of these types of media is of vital importance for the growth of the bacterial strains. Growth of the bacterial strains can also be accomplished on honey based agar plates.

The bacterial strains listed in table 1 are producers of diacetyl, hydrogen peroxide and organic acids such as lactic and acetic acid. All of these molecules have been shown to be present in honey and thus may attribute to the honeys antibacterial properties, taste and quality. These inhibitors together with bacteriocins and other antibacterial substances produced by the bacterial strains suggest the production of broad-spectrum protein antagonists against other species of bacteria and yeasts. The bacterial strains are very potent inhibitors of yeasts belonging to the genus *Saccharomyces* which are commonly found in honey. Because of honeys extreme sensitivity to yeast, it can be expected to ferment even with only 1 spore per gram of honey if its water content is above about 18%. The preservation of honey by the bacterial strains described is thus crucial for the long-term storage of honey. The preservation capabilities of the bacterial strains listed in table 1 renders them useful in many preservation applications, not only for the preservation of honey but also for the preservation of food and beverages in general. The bacterial inhibition is effective against many bacteria such as against food spoilage and food-borne pathogenic microorganisms including *Clostridium tyrobutyricum*, *Staphylococcus aureus*, *Escherichia coli* and *Pseudomonas fluorescens*, *Lactobacillus sakei*, *Bacillus cereus*, *Listeria inocua*, *Enterococcus faecalis*, *Saccharomyces cerevisiae*, *Paenibacillus larvae*.

The invention also relates to isolated, pure cultures of the bacterial strains presented in table 1. Such pure cultures may be provided as colonies on agar plates, as liquid cell suspension or as a frozen, spray-dried or freeze-dried preparation. The cultures may be used alone or in combination in any application, such as in a food or beverage product, feed product or medical product. Further, the culture may contain and may be used to produce metabolites, antibacterial compounds and/or bacteriocins, which can be used in a variety of products or compositions, such as exemplified above.

Further, the products or compositions according to the invention may comprise two or more different strains of bacteria listed in table 1. By combining at least two or more of the strains the effects of the bacteria will be utilized in a synergistic manner so that more species of pathogens will be combated. Further, the efficiency of the products will be enhanced since many different bacteriocins will be produced. Consequently, a more naturally occurring mixture of bacterial strains as the naturally occurring mixture in the honey stomach and fresh honey will be obtained.

The product may contain a sugar source, wherein the sugar source is selected from the group comprising honey, sugar, fructose, sucrose, dextrine, maltose or glucose. By producing a product containing the bacterial strains according to the invention in combination with honey the bacterial strains will perform their functions in a synergistic manner with the honey. Therefore, it may be desirable to combine the effects of honey with added bacterial strains according to the invention.

Food or Beverage Product

A product or composition of the invention comprises at least one strain according to the invention and may be prepared in the form of a food or beverage product by using suitable food or beverage components or nutrients. The food or beverage can be used as a probiotic, prebiotic or symbiotic composition or product.

By the addition of one or more of the bacterial strains according to the invention new and improved products are obtained. These products may contain live, freeze dried or killed bacteria. Further the product may contain metabolites and/or bacteriocins produced by the bacteria. A product containing freeze dried bacterial strains can be activated by the addition of water.

By using the bacterial strains according to the invention a highly natural product may be produced. By combining at least two or more of the bacterial strains of the invention the effects of the bacteria may be utilized in a synergistic manner. In this way a more naturally occurring mix of bacterial strains as in honey may be obtained. The use of a mixture of bacterial strains also increases the chance of knocking out various undesirable pathogens.

A product may comprise a sugar source selected from the group comprising honey or for example sugar, fructose, sucrose, maltose and glucose. By producing a product or composition containing at least one bacterial strain according to the invention in combination with a sugar source such as honey the bacterial strains will perform their functions in a synergistic manner with the sugar source. It is desirable to combine the effects of honey with added bacterial strains according to the invention. According to one embodiment honey and bacteria containing beverages such as a honey water beverage can be prepared. The honey water beverage can be prepared by mixing water, honey, bacterial strains according to the invention and a fruit juice such as lemon juice, lime juice, orange juice or apple juice. The concentration of bacterial strains in the beverage may be from about $10^1$ to $10^{14}$ CFU/g product, such as $10^1$, $10^2$, $10^3$, $10^4$, $10^5$, $10^6$, $10^7$, $10^8$, $10^9$, $10^{10}$, $10^{11}$, $10^{12}$ or $10^{13}$ CFU/g product. This concentration of bacterial strains can also be used in a beverage product without added honey. A concentration about $10^5$ CFU/g product may be used in a product mimicking the naturally occurring concentration of bacterial strains in fresh honey. The honey water beverage may also be prepared in form of a concentrate, with less or no water content and with freeze dried bacterial strains and juice as mentioned before.

A honey food product may further be used as an ingredient for the production of other food products.

It is an aim of the invention to make use of food or beverages containing bacterial strains more easily accessible to, frequent and usual with any consumers, for the purpose of increasing, supplementing and balancing the intestinal flora, which will bring about advantages in terms of everyday health and sports activity.

According to another embodiment functional food or beverages containing mixtures of bacterial strains are provided, which are capable of reaching the intestines in a live or viable form and also their bacteriocins and/or metabolites, settling in the bacterial flora, influencing or growing, thereby performing important beneficial actions for the human health. The bacterial strains reaching the intestine may also be in a non live state, then performing a beneficial action via their produced bacteriocins and/or metabolites. The food or beverage may be used for the prevention and/or treatment of gastrointestinal diseases.

Examples of beverages are milk products, juice products, wine, vinegar, Swedish Glögg, beer, soda, lemonade and cider products. A beverage comprising one or more bacterial strains according to the invention and the addition of honey may be in form of honey water against cold or sour throat, as recovery for athletes, stressed persons or for recovery for immune suppressive hospital patients. A beverage may be characterized by its special constitution with minerals and other substances that give the desired natural effect as in fresh honey.

The beverage or food with added bacterial strains according to the invention will benefit from the conserving effect of the bacterial strains. Yeast fermentation will be strongly inhibited. Further, the bacterial strains can be used in wine-production for ending the yeast fermentation. The bacteria will sustain as a naturally originating health benefiting bacteria in the product.

The food or beverage may also contain additives such as way of examples vitamins, minerals, antioxidants, phenols, fibres, oligosaccharides, fructooligosaccharides or innulin.

Examples of food products are meat products, dairy products, fruit products, fish products, bakery products or vegetable products. A food product may contain a sugar source such as honey. The food product can be fresh honey or mature honey with added bacteria according to the invention. The honey food product can be prepared by adding the bacterial strains according to the invention or a mixture of bacterial strains according to the invention to the honey or other products. The concentration of bacterial strains can be suitably selected so as to achieve a concentration from about $10^1$ to $10^{14}$ CFU/g product such as $10^1$, $10^2$, $10^3$, $10^4$, $10^5$, $10^6$, $10^7$, $10^8$, $10^9$, $10^{10}$, $10^{11}$, $10^{12}$ or $10^{13}$ CFU/g product.

The bacterial strains according to the invention may also be used as starter cultures for the fermentation of food and beverages. Examples of food and beverages are bred, buttermilk, cacao, vanilla, coffee, cheese, green cheese, cucumbers, feed additives, fermented fish products, fermented milks, olive oil, sauerkraut, sausages, yoghurt, wine, beer, cider and honey.

Medical Product

A bacterial strain according to the invention is valuable for preventing or treating infections as it inhibits growth of pathogenic microorganisms. The strains and the products containing them may be transferred to the human or animal skin in forms such as ointments, creams, sprays, gels and liquid solutions. The bacterial strains may also be included in products such as dressings, dermal patches, gels, or bandages containing effective amounts of bacterial strains in various parts of the products so as to achieve the desired result of preventing or inhibiting infections. The products may be used for the treatment of wounds, sores, burns, scars, bed sores, diabetic lesions, acne, eczema, dermatitis, cancer, catarrh, rash, yeast infections, toxic shock syndrome, fungal infections, viral infections and ulcers.

The product may be used in the treatment of bacterial, viral, yeast or fungal infections. Viral infections of interest may be herpes virus infections including *Herpes labialis*. Bacterial infections to be combated by the bacterial strains according to the invention may be infections by species selected from the group comprising *Staphylococcus* species, *Clostridium* species, *Bacillus* species, *Enterococcus* species, *Pseudomonas* species, *Listeria* species and *Escherichia coli*.

The medical products may include the bacterial strains according to the invention in combination with a sugar source such as honey or synthetic honey. The product will then benefit from known effects of honey in combination with the effects of the bacterial strains. The product may include varying percentages by weight of creamed or crystallised honey, spray dried, freeze dried, air dried honey and/or liquid honey. The honey may be fresh or mature.

The medical product may include the metabolites and/or bacteriocins produced by the bacterial strains according to the invention. This product may additionally be sterilised in a known manner in order to achieve a sterile product without any viable bacteria. The product will benefit from the bacteriocins and/or metabolites previously produced by the bacterial strains.

The active ingredients i.e. live or dead bacterial strains and bacteriocins and/or metabolites may comprise about 0.1% to about 100%, such as 1% to 70%, such as 5% to 50% by weight of the final product. A typical product will contain in a one gram dosage formulation a concentration of from $10^1$ to $10^{14}$ CFU, such as $10^1$, $10^2$, $10^3$, $10^4$, $10^5$, $10^6$, $10^7$, $10^8$, $10^9$, $10^{10}$, $10^{11}$, $10^{12}$ or $10^{13}$ CFU of viable or killed bacteria.

The medical product may include at least one or more of the bacterial strains of the invention or bacteriocins produced from one or more of the bacterial strains according to the invention. A mixture of bacterial strains or bacteriocins from different bacterial strains may be beneficial regarding the pathogen inhibition efficiency.

The medical product may also include the bacterial strains in a chewing gum. This product can be used in the treatment of for instance gingivitis and plaque. Ingredients of a chewing gum product can be one or more of honey, bees wax, gum and other ingredients known in the art.

Optional ingredients in the medical product include pharmaceuticals such as antibiotics, fungicides and other antibacterial agents, vitamins, buffering agents, coloring agents, minerals, flavorings, fragrances, gelling agents or other chemical compounds such as antioxidants or calcium.

The medical product may include a base material in the form of a film, woven dressing, layered sheet dressing, patch, strap, rope configuration or wrap. Options for the base material include agar gel film, alginate dressing, hydro-colloid, foam dressing, and so forth. Further the product may comprise the bacterial strains according to the invention along with pharmaceutically or physiologically acceptable carriers, excipients and/or diluents. Carriers for dry formulations may be trehalose, malto-dextrin, rice flour, micro-crystalline cellulose, magnesium stearate, inositol, and others. Liquid or gel-based carriers can be water, salt solutions, alcohols and the like. A medical product may then be formed by applying the bacterial strains to an absorbent or the like.

The medical product may be in form of a pharmaceutical product using pharmaceutically acceptable carriers together with the bacteria according to the invention. Examples of pharmaceutically acceptable carriers include various diluents and excipients such as fillers, extenders, binders, humectants, disintegrators, surfactants, lubricants and other carriers known in the art. The dosage may be in form of a pill, tablet, powder, solution, suspension, emulsion or granules. Tablets may be coated with a standard coating material. The amount of bacterial strains in the pharmaceutical product may be selected from about $10^5$ to $10^{14}$ CFU/dosage of the product, such as $10^5$, $10^6$, $10^7$, $10^8$, $10^9$, $10^{10}$, $10^{11}$, $10^{12}$ or $10^{13}$ CFU. The medical product may be used for the prevention and/or treatment of gastrointestinal diseases.

Feed Product

The bacterial strains according to the invention may be valuable in feed products for bee and bee larvae. These products may be in form of a probiotic feed used to strengthen or re-establishing the microbial flora within the bee or bee larvae. The used bacterial strains are naturally occurring bacterial strains in the honey producing tract of a bee. Thus, the bacterial strains according to the invention will not knock out any naturally occurring bacterial strains within the honey producing tract niche. The usage of other beneficial bacterial strains not originating from the honey producing tract, in similar products, could alter the natural bacterial flora of the honey bee in a negative matter. Therefore this type of feed product according to the invention will be particularly interesting.

The feed product may include one or several of the bacterial strains listed in table 1. A mixture of bacterial strains may be beneficial regarding the treatment efficiency.

The concentration of bacterial strains can be suitably selected so as to achieve a concentration from about $10^1$ to $10^{14}$ CFU/g product such as $10^1$, $10^2$, $10^3$, $10^4$, $10^5$, $10^6$, $10^7$, $10^8$, $10^9$, $10^{10}$, $10^{11}$, $10^{12}$ or $10^{13}$ CFU/g product.

The feed product may be used for the protection of honey bee or honey bee larvae from pathogenic bacteria, virus, fungus or mite. Organisms commonly leading to lethal infections and to be combated by the product are *Paenibacillus larvae*, *Melissococcus plutonius*, *Ascosphaera apis*, *Varroa destructor*, deformed wing virus or *Nosema apis*.

The bacterial strain or bacterial strain mixture may be administered to the honey bees or honey bee larvae as a powder, solution or as a solid. A powder may be in a freeze dried, spray dried or air dried form. A powder is simple to handle, transport, store and has a more expanded date of expiration. The powder or solution may be sprinkled or sprayed over the honey bees or larvae. Effective administration may also be accomplished by spraying or sprinkling a powder or solution directly over the honey bee nest.

The feed product may also contain a sugar source. The sugar source can be honey, sugar, sucrose, glucose, fructose, dextrine, maltose or other forms of sugar. The sugar source may be used by the honey bee or honey bee larvae as an energy source. By using honey in the sugar solution several advantages are gained. Firstly, the bees are more eager to use a honey containing solution than a plain sucrose containing solution. Secondly, honey contains additional beneficial components such as minerals, vitamins and proteins.

When using the bacterial strains according to the invention a honey bee feed containing them will benefit from the bacteria and yeast inhibition properties of the bacteriocins and metabolites. Consequently, the sugar solution will not ferment as is normally the case for sugar solutions.

The feed product may also contain pollen, soybean, bee bread or synthetic bee bread, important food sources for honey bees and honey bee larvae during autumn, winter and spring. The feed product may also contain other additives such as vitamins, minerals, fat, carbohydrates and proteins.

The administration of the bacterial strains is particularly important in autumn or winter when the honey bee societies are week and resting. The bacterial strains will also function as a preservative of the honey or sugar present in the society. In the period of autumn, winter and early spring when no nectar is available, the bees and bee larvae are particularly vulnerably to bacterial, viral, fungal and parasitic infections. By the administration of bacterial strains according to the invention to the honey bees and honey bee larvae, the bacteria will grow out to a viable state when they reach the honey bee honey producing tract which is their original natural environment. Thereby, the bee and larvae will have acquired a more efficient protection against honey bee and larvae pathogens.

Following examples are intended to illustrate, but not to limit, the invention in any manner, shape, or form, either explicitly or implicitly.

EXAMPLES

Example 1

Bee Hive Harvesting

A small bee hive with approximately 12.000 bees was transported to a field of wild raspberry flowers at the nature reserve Kullaberg situated at the North West of Skåne, in the south of Sweden. No other flowers in the immediate area were flowering during that time and the bee hive was emptied of its honey when the experiment was initiated. In the second week samplings were performed on fresh raspberry flowers around the bee hive, outgoing and incoming worker bees and fresh raspberry flower honey from the bee comb. In addition to those samples, harvested raspberry honey was saved and analysed after two months of storage. The samples were cultivated in four different types of incubation media for all bacterial purpose and for the selection of LAB. The bacterial identity was revealed by the analysis of 16S rRNA genes using both the techniques of cloning and pure cultures.

Example 2

Isolation of Bacteria from the Honey Bee 20 raspberry flowers, 10 incoming and 10 outgoing worker bees and 10 nurse bees were picked and sorted in different sterile 10 ml tubes containing 5 ml sterile physiological saline (0.9% w/v NaCl, 0.1% w/v Tween 80 and 0.1% w/v pepton). Moreover, 0.5 ml fresh honey, five honey bee larva (2-5 days old), five honey bee heads, five honey bee honey stomach and one honey bee hindgut, were collected separately in a 1.5 ml sterile micro tube containing 0.9 ml physiological saline. The analysis of the honey bee mouth and trunk was performed separating the head from the body with a sterile scalpel and tweezers. The heads were shaken in sterile dilution media followed by bacterial cultivation. The analysis of the honey bee stomach was carried out by excision of a with nectar full honey bee stomach after the oesophagus and before the proventriculus with sterile scalpel and tweezers which guaranteed that no parts of the intestine contaminated the samples. The tubes were shaken and immediately transported to the laboratory. Tubes with 0.5 ml suspension were frozen and stored at −20° C. for direct 16S rRNA gene analysis.

The bacterial strains listed in table 1 were isolated viable from the healthy honey bees. The flower nectar source resulting in highest number of bacteria according to the invention was found to be raspberry flower. Intestinal samples of bacterial strains demonstrated no numbers of the strains according to the invention.

Example 3

Culturing of Bacteria from the Honey Stomach

From the samples described in example 2 a dilution series with sterile physiological saline was made and a volume of 0.1 ml was spread on different growth media. Growth and pure cultures were obtained on different media (see Table 2) from different dilutions with Tryptone Soy Broth agar (TSB) (Oxoid, Basingstoke, Hampshire, England), Tomato juice agar (TJ) (Oxoid), all purpose medium with Tween® (APT) (Merck, Darmstadt, Germany) and Rogosa agar (Merck). The media were produced according to the manufacture's instructions. The used combination of isolation media were shown to be of vital importance for the growth of the bacteria. All the isolates grew very well on Rogosa except Bma5, which had a restricted growth and Fhon2 that barely grew on Rogosa. On the contrary, Fhon2 (*Lactobacillus kunkeei*) grew very well on Tomato juice agar together with the strains belonging to the genus *Bifidobacterium* (Bin2, Bin7, Bma6 and Hma3). The other *Lactobacillus* sp. (Biut2, Hon2, Hma2, Hma8, Hma11 and Bma5) had a restricted growth on Tomato juice agar. The isolates were cultivated both aerobically and anaerobically for 2-3 days at 37° C. Ten to thirty colonies were randomly picked from all media used, containing 30-300 colonies each, and re-cultivated for purity (isolates).

TABLE 2

Growth of bacteria on specific media

| Bacteria | Culturing media |
| --- | --- |
| *Bifidobacterium* strain Bin2 | Tomato, APT, Rogosa, TSB |
| *Bifidobacterium* strain Bin7 | Tomato, APT, Rogosa, TSB |
| *Lactobacillus* strain Biut2 | Tomato, APT, Rogosa, TSB |
| *Bifidobacterium* strain Hma3 | Tomato, Rogosa |
| *Lactobacillus* strain Hon2 | Tomato, APT, Rogosa |
| *Lactobacillus* strain Hma8 | Tomato, Rogosa, APT |
| *Bifidobacterium* strain Bma6 | Tomato, TSB, Rogosa |
| *Lactobacillus* strain Bma5 | Tomato, Rogosa, APT |
| *Lactobacillus* strain Hma2 | Tomato, Rogosa, APT |
| *Lactobacillus kunkeii* Fhon2 | Tomato, APT, TSB, Rogosa |
| *Lactobacillus* strain Hma11 | Tomato, Rogosa, APT |

Example 4

Cloning and PCR-Amplification

One colony from the purified isolates was placed in 0.2 Thermo-Strips (Abgene, Surrey, UK) together with 0.1 ml sterile water and glass beads (0.106 mm, Sigma-Aldrich, St Louis, USA). Cells were disintegrated by shaking for 45 min in a MS1 Minishaker (IKA Works, INC, Wilmington, USA). After centrifugation, 20200×g for 5 min in a Galaxy mini centrifuge (VWR, Pennsylvania, USA) 1 µl of the supernatant was used in the following PCR reaction.

Amplification was conducted with primers designed to anneal to conserved regions of bacterial 16S rRNA genes. The forward primer ENV1 (5'-AGA GTT TGA TII TGG CTC AG-3') corresponded to positions 8-27 to *Escherichia coli* 16S rRNA, and the reverse primer ENV2 (5'-CGG ITA CCT TGT TAC GAC TT-3') corresponded to positions 1511-1492 (Brosius et al., 1978). The PCR reaction contained 5 µl 10×PCR buffer (100 mM Tris-HCl, 15 mM $MgCl_2$, 500 mM KCl, pH 8.3), 200 µmol $l^{-1}$ of each deoxyribonucleotide triphosphate, 2.5 U of Taq DNA polymerase (Roche Diagnostics, Mannheim, Germany), 10 pmol of each primer and 1-10 µl template in a total volume of 50 µl. Amplification was performed with a Mastercycler (Eppendorf, Hamburg, Germany) as follows: 30 cycles at 95° C. for 15 s, 48° C. for 30 s and 72° C. for 90 s followed by an elongation step at 72° C. for 10 min. The PCR product was stored at −20° C. for sequencing.

In accordance with the procedure for the EZ1 DNA Tissue Kit (Qiagen, Hilden, Germany), 190 µl Buffer G2 and 10 µl Proteinase K were added to the pellet and mixed with a MS1 Minishaker for 2 min. The samples were incubated in a 56° C. water bath (Julabo SW1, Germany) until the pellets were dissolved. Every 15 min the samples were mixed for 1 min to speed up the process. Glass beads (0.106 mm) were added and cells were disintegrated by shaking for 45 min in a MS1 Minishaker. After centrifugation, 20200×g for 5 min in a Galaxy mini centrifuge. 0.1 ml of the supernatant was further treated in accordance with the procedure for the EZ1 DNA Tissue Kit in a BioRobot EZI version 1.3 (Qiagen Instruments AG, Germany), using the tissue card from Qiagen. At the end of the process the DNA was eluted in 200 µl sterile water.

PCR amplifications were performed in four duplicates for each sample to minimise PCR-introduced biases. Amplification was carried out in the same way as for the isolates but with an annealing temperature of 50° C. The four PCR products from each DNA preparation were pooled together and checked by running them on 1.5% (w/v) agarose gels (Type III, High EEO, Sigma, ST. Louis, USA). Gels were stained with ethidium bromide and visualised in UV light.

The pooled PCR products were purified by GFX™ PCR DNA and Gel Band Purification Kit (Amersham Biosciences, UK). The purified products were ligated into a TOPO TA cloning vector (Invitrogen, USA) and transformed into competent pCR II-TOPO *E. coli* cells in accordance with the manufacturer's instructions. Colonies were blue/white screened on LB agar with Kanamycin (Sigma) and X-gal (Promega). Twenty-four white colonies were randomly chosen from each sample and re-cultivated.

In order to recover the cloned DNA, amplification was carried out with universal primers M13 forward (5'-GTA AAA CGA CGG CCA G-3') and M13 reverse (5'-CAG GAA ACA GCT ATG AC-3') designed to anneal at the beginning and end of the vector. The PCR reaction contained 5 µl 10×PCR buffer (100 mM Tris-HCl, 15 mM $MgCl_2$, 500 mM KCl, pH 8.3), 200 µmol $l^{-1}$ of each deoxyribonucleotide triphosphate, 2.5 U of Taq DNA polymerase (Roche Diagnostics, Mannheim, Germany), 10 pmol of each primer and 1-10 µl template in a total volume of 50 µl. Amplification was performed with a Mastercycler (Eppendorf, Hamburg, Germany) using one denaturing step at 94° C. for 10 min followed by 28 cycles at 94° C. for 1 min, 55° C. for 1 min and 72° C. for 1 min, followed by an elongation step at 72° C. for 10 min. The PCR product was stored at −20° C. for sequencing.

Example 5

16S rRNA Sequencing and Phylogenetic Analysis

PCR products originating from bacteria isolated were sequenced by a sequencing company (MWG Biotech AB, Ebersberg, Germany) with universal primers ENV1 and ENV2. These partial 16S rRNA sequences were searched against GenBank (National Centre for Biotechnology Information, Rockville Pike, Bethesda, Md.) using the Advanced BLAST similarity search option (Altschul, S. F., et al. *Nucleic Acids Res* 25, 3389-3402), accessible from the homepage of the National Centre for Biotechnology Information (http://www.ncbi.nlm.nih.gov/). For comparison, sequences were also searched against another software, the Ribosomal Database Project II, accessible from the homepage (http://rdp.cme.msu.edu). The partial sequences were around 1400 base pairs (range 50-1500 bp).

The phylogenetic tree in FIG. 1 was obtained using the following computer software programs: Clustal X (version 1.81) (Thompson, J. D., et al. 1997. *Nucleic Acids Res* 24, 4876-4882) for alignment, BioEdit (version 6.0.7) (Hall, T., BioEdit Sequence Alignment Editor, Isis Pharmaceuticals, Inc) for editing, and PAUP (version 4.0 beta) (written by D. Swofford) for computing the phylogenetic tree. The tree was constructed using the neighbour-joining method (Saitou, N. and Nei, M. 1987. *Mol Biol Evol* 4, 406-425) in PAUP with the evolutionary distance estimation LogDet/Paralinear model.

Example 6

Fermentation Patterns

The API 50CHL (BioMerieux SA, France) system was used to tentatively identify the bacterial strains by their carbohydrate fermentation patterns, see table 3. Cultures on tomato juice agar were harvested and re suspended in the suspension medium provided with the kit. API strips were inoculated and analysed (after 48 and 82 h) according to the manufacturers instructions.

TABLE 3

Fermentation patterns

| API no | Active Ingredients | Hon2 | Hma2 | Biut2* | Hma8 | Bma5 | Fhon2 | Hma3 | Bin2 | Bin7 | Bma6 |
|---|---|---|---|---|---|---|---|---|---|---|---|
| 0 | Control | + | + | + | + | + | + | + | + | + | + |
| 1 | Glycerol | − | − | − | − | − | − | − | − | − | − |
| 2 | Erythritol | − | − | − | − | − | − | − | − | − | − |
| 3 | D-Arabinose | − | − | − | − | − | − | − | − | − | − |
| 4 | L-Arabinose | + | − | − | − | − | − | + | + | + | − |
| 5 | D-Ribose | + | − | − | +/− | − | − | + | + | + | + |
| 6 | D-Xylose | − | +/− | − | − | − | − | + | + | + | − |
| 7 | L-Xylose | − | − | − | − | − | − | − | − | − | − |
| 8 | D-Adonitol | − | − | − | − | − | − | − | − | − | − |
| 9 | Methyl-βD-Xylopyranoside | − | − | − | − | − | − | − | − | − | − |
| 10 | D-Galactose | − | − | + | − | − | − | + | + | + | − |
| 11 | D-Glucose | + | − | + | + | + | + | + | − | + | + |
| 12 | D-Fructose | + | − | + | +/− | + | + | + | − | − | − |
| 13 | D-Mannose | − | − | − | +/− | + | − | − | − | − | + |
| 14 | L-Sorbose | − | − | − | − | + | − | − | − | − | − |
| 15 | L-Rhamnose | + | − | − | − | − | − | − | − | − | − |
| 16 | Dulcitol | − | − | − | − | +/− | − | − | − | − | − |
| 17 | Inositol | − | − | − | − | − | − | − | − | − | − |
| 18 | D-Manitol | + | − | − | − | − | +/− | − | − | − | − |
| 19 | D-Sorbitol | − | − | − | − | + | − | − | − | − | − |

TABLE 3-continued

Fermentation patterns

| API no | Active Ingredients | Hon2 | Hma2 | Biut2* | Hma8 | Bma5 | Fhon2 | Hma3 | Bin2 | Bin7 | Bma6 |
|---|---|---|---|---|---|---|---|---|---|---|---|
| 20 | Methyl-αD-Mannopyranoside | − | − | − | − | − | − | − | − | − | − |
| 21 | Methyl-αD-Glucopyranoside | − | − | + | − | − | − | − | − | − | − |
| 22 | N-Acetyl Glucose amine | + | + | + | + | + | − | − | − | − | − |
| 23 | Amygdalin | − | − | − | − | + | − | − | − | − | +/− |
| 24 | Arbutin | +/− | − | + | − | + | − | +/− | − | + | +/− |
| 25 | Esculin Ferric citrate | + | + | − | − | + | − | + | + | + | + |
| 26 | Salicin | − | − | + | − | +/− | − | + | + | + | +/− |
| 27 | D-Cellobiose | − | − | +/− | − | + | − | + | − | + | + |
| 28 | D-Maltose | + | − | + | +/− | − | − | + | − | − | + |
| 29 | D-Lactose (bovine origin) | − | + | − | − | − | − | + | − | − | − |
| 30 | D-Melibiose | − | − | − | − | − | − | − | + | + | − |
| 31 | D-Saccharose (sucrose) | + | − | − | − | +/− | + | +/− | − | +/− | − |
| 32 | D-Trehalose | + | − | + | − | − | + | + | − | − | − |
| 33 | Inulin | − | + | − | − | − | − | − | − | − | − |
| 34 | D-Melezitose | +/− | − | − | − | − | − | − | − | − | − |
| 35 | D-Raffinose | − | +/− | − | − | − | − | + | − | + | − |
| 36 | Amidon (starch) | − | − | +/− | − | − | − | − | − | − | − |
| 37 | Glycogen | − | − | − | − | − | − | − | − | − | − |
| 38 | Xylitol | − | − | − | − | − | − | − | − | − | − |
| 39 | Gentiobiose | − | − | + | − | − | − | − | − | − | + |
| 40 | D-Turanose | + | − | − | − | − | − | − | − | − | − |
| 41 | D-Lyxose | − | − | − | − | − | − | − | − | − | − |
| 42 | D-Tagatose | − | − | + | +/− | − | − | − | − | − | − |
| 43 | D-Fucose | − | − | − | − | − | − | − | − | − | − |
| 44 | L-Fucose | − | − | − | − | − | − | − | − | − | − |
| 45 | D-Arabitol | − | +/− | − | − | − | − | − | − | − | − |
| 46 | L-Arabitol | − | − | − | − | − | − | − | − | − | − |
| 47 | Potassium Gluconate | − | − | − | − | − | +/− | − | − | − | − |
| 48 | Potassium 2-Ketogluconate | − | − | +/− | − | − | − | − | − | − | − |
| 49 | Potassium 5-Ketogluconate | − | +/− | − | − | − | +/− | − | − | − | − |

*= The CHL-media was supplemented with 5% W/V casamino acids suspended in sterile water and sterile filtered.

Example 7

Fermentation Patterns and DNA-Fingerprinting of the L. kunkeei Type Strain and of L. kunkeei Strain Fhon2

The API 50CHL (BioMerieux SA, France) system was used to compare the strain Fhon2 and the type strain *L. kunkeei* type strain YH-15 by their carbohydrate fermentation patterns. Cultures on tomato juice agar were harvested and re suspended in the suspension medium provided with the kit. API strips were inoculated and analysed (after 48 and 82 h) according to the manufacturers instructions. The results diverged in that *L. kunkeei* type strain YH-15 could ferment D-Raffinose which Fhon2 could not and in that Fhon2 could ferment D-Trehalose, Potassium Gluconate and Potassium 5-Ketogluconate which *L. kunkeei* type strain YH-15 cold not. It evidenced that the bacterial strain according to the invention including *Lactobacillus kunkeei* Fhon2 differ from the *Lactobacillus kunkeei* type strain.

Figure 2:
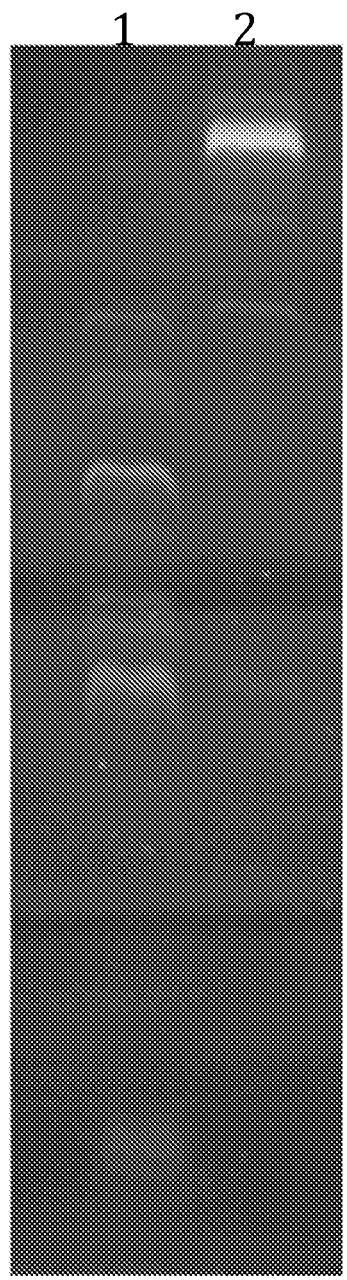
FIG. 2 illustrates RAPD patterns of the type strain *Lactobacillus kunkeei* (sample 1) and *fLactobacillus kunkeei* Fhon 2 (sample 2).

Randomly amplified polymorphic DNA (RAPD) analysis was used to distinguish *Lactobacillus kunkeei* Fhon 2 from the *Lactobacillus kunkeei* type strain. The laboratory procedure was performed according to Jansson D S et al., 2004. *J Med Microbiol.* 53, 293-300, using primer 1254 (5'-CCG-CAGCCAA-3'). The result of RAPD patterns obtained with primer 1254 is shown in FIG. 2. It evidenced that the RAPD pattern of the bacterial strains according to the invention including *Lactobacillus kunkeei* Fhon 2 differ from the *Lactobacillus kunkeei* type strain. Identical bacterial strains should show identical patterns in the agarose gel relating to the bacterial chromosome composition. The *Lactobacillus kunkeei* type strain indicated by number 1 in FIG. 2 shows 9 DNA-bands and *Lactobacillus kunkeei* Fhon 2 indicated by number 2 shows 6 DNA-bands. The strains have different band numbers and also different band patterns which means that they differ in the composition of the whole DNA genome.

Given the above, *Lactobacillus kunkeei* Fhon 2 is a novel *Lactobacillus kunkeei* strain in spite of the high 16S rRNA similarity between *Lactobacillus kunkeei* Fhon 2 and the type strain displayed in the phylogenetic tree in FIG. 1.

Example 8

Bee Hive Infection

One of the bee hives was infected with the larvae pathogen *Paenibacillus larvae*. Infection by this pathogen will normally lead to a development of the lethal American Foul Brood disease (AFB). After infection the bee hive was placed beside a field of raspberry flowers and Linden trees whose nectar work as a prebiotic for the bacteria according to the invention. At this point the numbers of *P. larvae* started to decrease from its recorded maximum of eight billion CFU per larvae and vanished three weeks later without developing AFB. This result showed very clearly that the bacterial strains according to the invention can together fight this pathogen when they are fed with nectar as from raspberry and linden flowers containing more fructose than other nectars.

Example 9

Probiotic Feed for Bee and Bee Larvae, Autumn

A honey bee feed product for autumn (bee winter rest) constituting freeze dried bacteria according to the invention and a sugar source was prepared by mixing the bacteria with a sugar solution containing 19% fructose, 19% glucose, 37% sucrose and 25% water. The total amount of product used was 16 kg/honey bee society and the product contained $10^5$ CFU bacteria/g product. The ingredients were mixed and fed to be societies in a bottle on top of the bee society. The bees ingested the solution and stored it in their honey comb cells with a wax sealing.

In a second application, the freeze dried bacteria were mixed with 1 kg of honey leading to a bacterial CFU concentration of $10^7$ per gram product. 1 kg honey was mixed with 13 kg sucrose and 14 kg water. This product having a sugar content around 50% like flower nectar and a bacterial CFU similar to that in the honey stomach. The sugar solution was left standing for one day before administration to the bees. In this way the freeze dried bacteria had a chance to wake up and start to multiply and produce beneficial metabolites and bacteriocins before use. The sugar solution was not yeast fermented as is normally the case when using sugar solutions without added bacteria. By using honey in the sugar solution several advantages were gained. Firstly, the bees were more eager to use the sugar solution than with plain sucrose. Secondly, honey contains additional components such as minerals, vitamins and proteins.

Example 10

Preservation Study $4 \times 10^7$ CFU *Lactobacillus kunkeei* strain Fhon2 was mixed with 200 ml water, 5 ml lemon juice and 17 ml honey. The honey water was left in a refrigerator for three weeks. After three weeks the water tasted fresh without a taste of fermentation or bacteria. The amount of *Lactobacillus kunkeei* was doubled and yeasts could not be detected.

Example 11

Sugar Resistance Study

Figure 3:
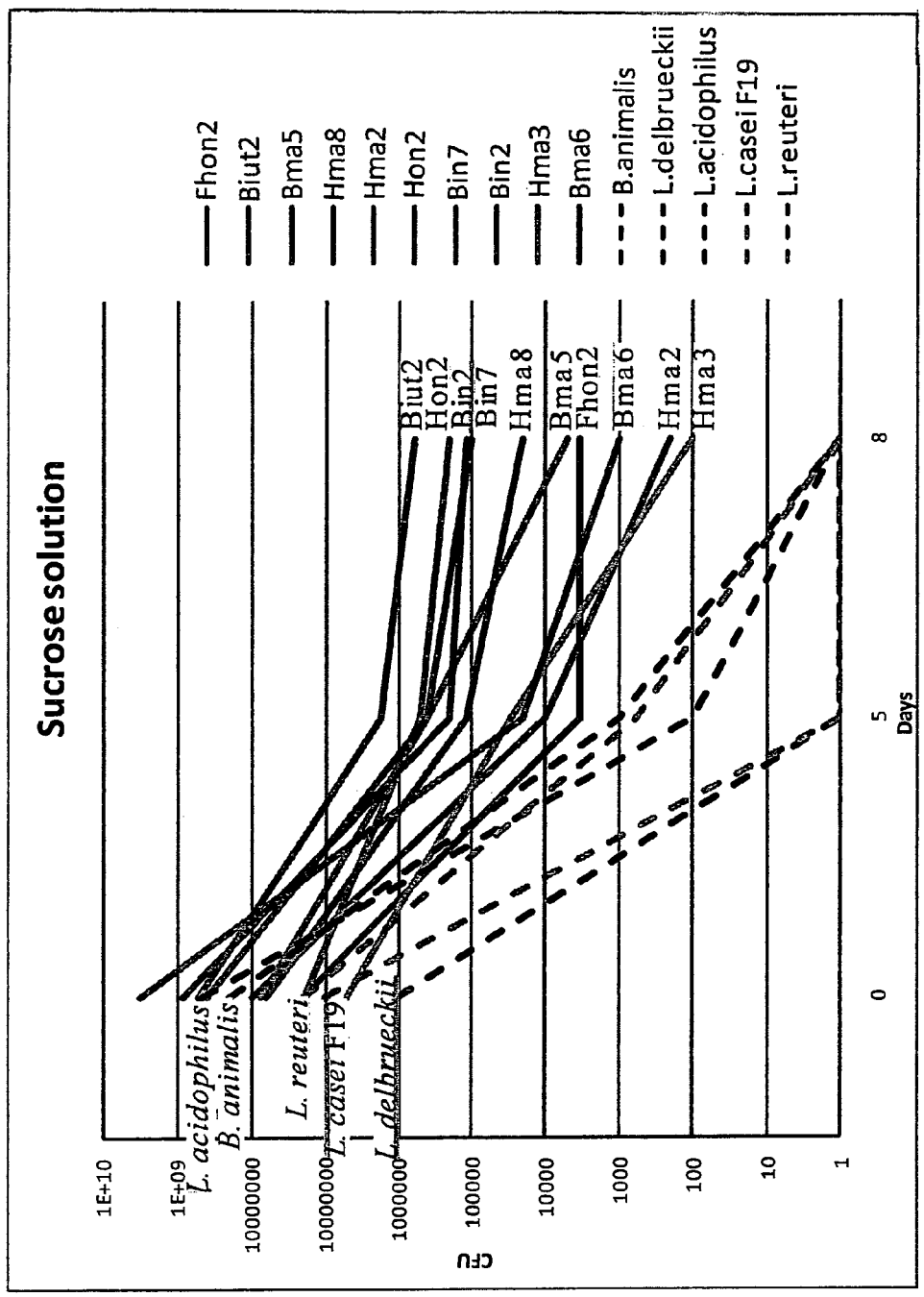
FIG. 3 illustrates sugar resistance of different strains in a 65% sugar solution containing 65% sucrose and 35% water.

The bacterial strains according to the invention and the commercial available product strains *L. acidophilus* DSM 20079, *L. casei* JCM 1134, *L. reuteri* DSM 20016, *B. animalis* subsp. *lactis* DSM 10140 and *Lactobacillus delbrueckii* subsp. *bulgaricus* DSM 20081 were mixed in separate vials with a sugar solution containing 65% sucrose and 35% water. The final sugar concentration was 65%. The vials were incubated at 22° C. and viable counts were performed. The results demonstrated that the bacterial strains according to the invention were much more sugar resistant (after 8 days all were still viable in cfu numbers between $10^2$ and $10^5$ cfu per ml) than the commercially available product strains (all of them were dead after 8 days), see FIG. 3

Figure 4:
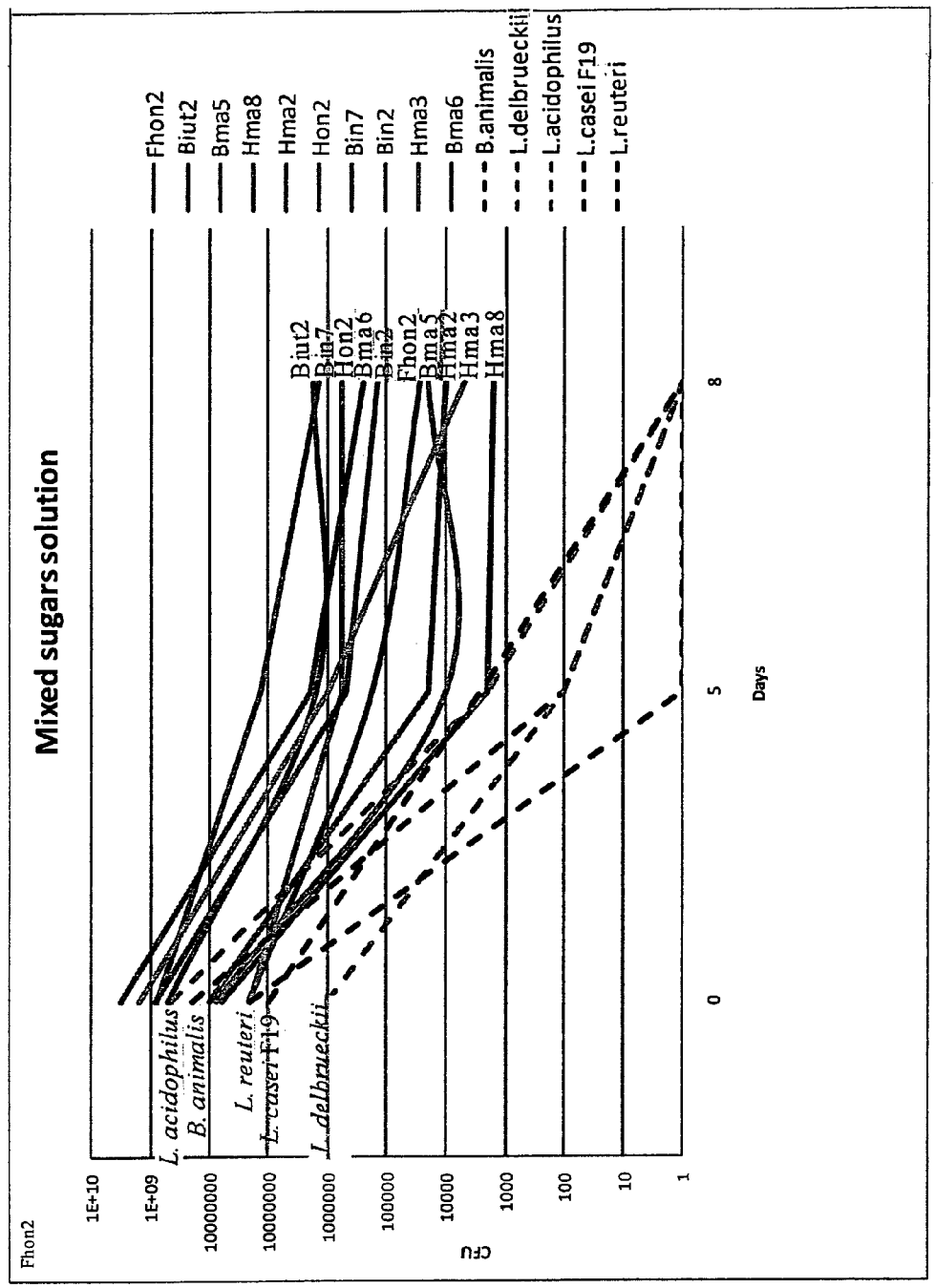
FIG. 4 illustrates sugar resistance of different strains in a 70% sugar solution containing 19% fructose, 19% glucose, 37% sucrose and 25% water.

A second trial was performed repeating the first one but with a different sugar solution containing 19% fructose, 19% glucose, 37% sucrose and 25% water. In this solution the sugar concentration was 70% which is a very high sugar concentration for bacteria. Again the results demonstrated that the bacterial strains according to the invention were much more sugar resistant (after 8 days all were still viable in cfu numbers between $10^3$ and $10^6$ cfu per ml) than the commercially available product strains (all of them were dead after 8 days), see FIG. 4.

Example 12

Pathogen- and Food Spoiling-Microorganism Inhibition Study

The bacterial strains according to the invention were screened against the food and honey spoiling yeast *Saccharomyces cerevisiae*, the food spoiling bacteria *Pseudomonas fluorescens* and *Clostridium tyrobutyricum*, *Lactobacillus sakei*, *Bacillus cereus*, *Listeria inocua* and the human pathogens *Escherichia coli*, *Enterococcus faecalis* and *Staphylococcus aureus* where also *Pseudomonas* as a genus is represented, in this case as *Pseudomonas fluorescens* even if this species is not a pathogen, and the honeybee pathogen *Paenibacillus larvae*. The bacterial strains according to the invention were cultivated on MRS broth containing 0.5% L-cystein (except Fhon2 that was cultivated on MRS broth containing 2% fructose) anaerobically at 35° C. for three days and continued growths were obtained separately in the centre of MRS agar plates containing 0.5% L-cystein (except Fhon2 that was cultivated on tomato juice agar plates) anaerobically at 35° C. for one day. The test strains in table 4 were cultivated on liquid media, according to table 4, and then mixed with new media containing 0.8% agar) at a temperature of 42° C. The media and bacteria were mixed and poured over the plates with the cultivated bacterial strains according to the invention. The plates were then incubated at 35° C. for 3 days and analyzed for inhibition zones, wherein the diameter of the zone was measured in cm.

TABLE 4

Inhibition of pathogen- and food spoiling-microorganisms

| Strain | Cult. Media | Bin2 | Hma2 | Hon2 | Hma3 | Hma8 | Bin7 | Bma6 | Biut2 | Bma5 | Fhon2 | Hma11 |
|---|---|---|---|---|---|---|---|---|---|---|---|---|
| *S. cerevi* | MRS | | 2 cm | | | * 2 cm | | | 2 cm | 2 cm | | |
| *P. fluoresc.* | BHI | 2 cm | 2 cm | 2 cm | 2 cm | 2 cm | 2 cm | 2 cm | 2 cm | 2 cm | 1 cm | |
| *E. coli* | BHI | 2 cm | 2 cm | 2 cm | 2 cm | 2 cm | 2 cm | 2 cm | 2 cm | 2 cm | 2 cm | |
| *Cl. tyrobut.* | RCM | 2 cm | 2 cm | 2 cm | 2 cm | 2 cm | 2 cm | 2 cm | 2 cm | 1 cm | 1 cm | |
| *S. aureus* | BHI | 2 cm | 2 cm | 2 cm | 2 cm | 2 cm | 2 cm | 1 cm | 2 cm | 2 cm | 1 cm | |
| *E. faecalis* | M17 | | 1 cm | | | 1 cm | | | 1 cm | 1 cm | | |
| *L. sakei* | MRS | | 1 cm | | | 1 cm | | | 1 cm | 1 cm | 1 cm | |

TABLE 4-continued

Inhibition of pathogen- and food spoiling-microorganisms

| Strain | Cult. Media | Bin2 | Hma2 | Hon2 | Hma3 | Hma8 | Bin7 | Bma6 | Biut2 | Bma5 | Fhon2 | Hma11 |
|---|---|---|---|---|---|---|---|---|---|---|---|---|
| B. cereus | BHI | | | | | | | | | | 1 cm | |
| L. inocua | M17 | | | | | | | | | | 1 cm | |
| P. larvae | MYPGP | 1 cm | 4 cm | 2 cm | 2 cm | 4 cm | 3 cm | | 3 cm | 4 cm | 2 cm | 2 cm |

* . . . cm stands for inhibition zone around the bacterial strains according to the invention when the test bacteria was cultivated on top of them.

The results demonstrated clearly the inhibition of the food spoilage or pathogenic bacteria with most often a zone of 2.0 cm meaning that those bacteria die or cannot grow in this sphaerical zone around the bacterial strains according to the invention. When *Lactobacillus kunkeei* Fhon2 and the *Lactobacillus kunkeei* type strain was tested for inhibition of the bee pathogen *Paenibacillus larvae* only *Lactobacillus kunkeei* Fhon2 inhibited the pathogen (table 4) but the *Lactobacillus kunkeei* type strain (not displayed in table 4) did not inhibit *P. larvae* at all. This results evidence again that *Lactobacillus kunkeei* Fhon 2 is a novel *Lactobacillus kunkeei* strain.

Example 13

Administration Study

The bacterial strains according to the invention were orally administrated to ten healthy individuals of different ages with no infections or any intestinal diseases. They had a washout period of one week before the administration, when no probiotic products were consumed. Administration was performed daily for 10 days. The ingested drink contained bacteria prepared from fresh cultures with a concentration equivalent to about $10^9$ CFU per strain, 20 ml oat milk. The volunteers delivered faecal samples that were taken directly before administration, after 10 days of administration and 7 days after the termination of the administration. One gram of faeces were serially diluted and plated on Rogosa agar. Six colonies from faecal samples were randomly picked and six were selected according to visual appearance. The isolate identification was achieved by RAPD.

Example 14

Synthetic Honey

Synthetic honey was manufactured adding various amounts of the strains in table 1 to a sugar solution containing the sugars, fructose, glucose sucrose, maltose and melezitose (originating for example from sugar beets, sugar canes or high fructose corn syrup) in various final concentrations as in natural flower nectars between 7 and 80%, together with amino acids, vitamins, minerals and water. The bacteria fermented the product for 3 days in 35° C. The water content was during the process lowered to below 18% as in natural honey.

Example 15

Synthetic Bee Bread

Synthetic bee bread was manufactured mixing synthetic honey, manufactured as in example 14 and containing the strains in table 1, and flower pollen or soy bean flour, baking a bee bread similar to the natural one made by honeybees of honey and pollen.

Example 16

Synthetic Honey for Wound Management

Synthetic honey was manufactured as in example 14, containing the strains in table 1 to be applied on wounds etc described under medical products. The synthetic honey can be used sterilized or with viable bacteria.

The invention claimed is:

1. A composition comprising a sugar source and all isolated bacterial strains selected from the group consisting of: *Lactobacillus* strain Biut2 (LMG P-24094), *Lactobacillus* strain Hma2 (LMG P-24093), *Lactobacillus* strain Hma8 (LMG P-24092), *Lactobacillus* strain Bma5 (LMG P-24090), *Lactobacillus* strain Hon2 (LMG P-24091), *Bifidobacterium* strain Bin7 (LMG P-23986), *Bifidobacterium* strain Hma3 (LMG P-23983), *Bifidobacterium* strain Bin2 (LMG P-23984), *Bifidobacterium* strain Bma6 (LMG P-23985), *Lactobacillus kunkeei* Fhon2 (LMG P-23987), and Hma11 (LMG P-24612), wherein each isolated bacterial strain is present in the composition at a concentration of $10^3$-$10^{13}$ cfu/g composition.

2. A pharmaceutical composition comprising the composition according to claim 1 and a pharmaceutically acceptable carrier or diluent.

3. The pharmaceutical composition according to claim 2, wherein said composition is a suspension, gel, cream, powder or capsule including the pharmaceutical composition of claim 2.

4. A pharmaceutical product comprising the pharmaceutical composition according to claim 2, wherein said product is a dressing, bandage or spray.

5. The composition of claim 1, wherein the sugar source is selected from the group consisting of honey, sugar, fructose, sucrose, dextrine, maltose or glucose.

6. A food or feed product comprising a sugar source and all isolated bacterial strains selected from the group consisting of: *Lactobacillus* strain Biut2 (LMG P-24094), *Lactobacillus* strain Hma2 (LMG P-24093), *Lactobacillus* strain Hma8 (LMG P-24092), *Lactobacillus* strain Bma5 (LMG P-24090), *Lactobacillus* strain Hon2 (LMG P-24091), *Bifidobacterium* strain Bin7 (LMG P-23986), *Bifidobacterium* strain Hma3 (LMG P-23983), *Bifidobacterium* strain Bin2 (LMG P-23984), *Bifidobacterium* strain Bma6 (LMG P-23985), *Lactobacillus kunkeei* Fhon2 (LMG P-23987), and Hma11 (LMG P-24612), wherein each isolated bacterial strain is present in the composition at a concentration of $10^3$-$10^{13}$ cfu/g composition.

7. A bee feed product comprising all isolated bacterial strains selected from the group consisting of: *Lactobacillus* strain Biut2 (LMG P-24094), *Lactobacillus* strain Hma2

(LMG P-24093), *Lactobacillus* strain Hma8 (LMG P-24092), *Lactobacillus* strain Bma5 (LMG P-24090), *Lactobacillus* strain Hon2 (LMG P-24091), *Bifidobacterium* strain Bin7 (LMG P-23986), *Bifidobacterium* strain Hma3 (LMG P-23983), *Bifidobacterium* strain Bin2 (LMG P-23984), *Bifidobacterium* strain Bma6 (LMG P-23985) and *Lactobacillus kunkeei* Fhon2 (LMG P-23987), and Hma11 (LMG P-24612), wherein
- each isolated bacterial strain is present in the composition at a concentration of $10^3$-$10^{13}$ cfu/g composition;
- the strain has the ability to inhibit growth of food spoilage and pathogenic microorganisms; and
- the strain has the ability to be viable for at least 8 days in a 65% by weight sugar solution.

8. The bee feed product according to claim 7, wherein the strain has the ability to be viable for at least 8 days in a 70% by weight sugar solution.

* * * * *